(12) United States Patent
Schaeffer

(10) Patent No.: US 8,821,532 B2
(45) Date of Patent: Sep. 2, 2014

(54) VASCULAR CLOSURE DEVICE

(75) Inventor: Darin G. Schaeffer, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 988 days.

(21) Appl. No.: 12/363,271

(22) Filed: Jan. 30, 2009

(65) Prior Publication Data

US 2010/0198254 A1   Aug. 5, 2010

(51) Int. Cl.
   *A61B 17/08* (2006.01)
   *A61D 1/00* (2006.01)
   *A61B 17/00* (2006.01)

(52) U.S. Cl.
   CPC ... *A61B 17/0057* (2013.01); *A61B 2017/00592* (2013.01); *A61B 2017/00668* (2013.01); *A61B 2017/00601* (2013.01); *A61B 2017/00623* (2013.01)
   USPC ........................................................ 606/213

(58) Field of Classification Search
   USPC ............... 606/139, 151, 200, 213; 623/23.72; 128/831, 842, 843
   See application file for complete search history.

(56) References Cited

U.S. PATENT DOCUMENTS

| | | | |
|---|---|---|---|
| 5,372,604 A * | 12/1994 | Trott | 606/232 |
| 5,445,167 A | 8/1995 | Yoon et al. | 128/898 |
| 5,478,353 A * | 12/1995 | Yoon | 606/213 |
| 5,501,696 A * | 3/1996 | Trott | 606/232 |
| 5,782,861 A | 7/1998 | Cragg et al. | 606/216 |
| 5,964,782 A | 10/1999 | Lafontaine et al. | 606/213 |
| 6,790,220 B2 | 9/2004 | Morris et al. | 606/213 |
| 7,060,084 B1 | 6/2006 | Loshakove et al. | 606/213 |
| 7,326,230 B2 | 2/2008 | Ravikumar | 606/213 |
| 7,396,359 B1 | 7/2008 | Derowe et al. | 606/213 |
| 7,833,238 B2 * | 11/2010 | Nakao | 606/151 |
| 8,556,934 B2 * | 10/2013 | Godin | 606/219 |
| 2006/0025784 A1* | 2/2006 | Starksen et al. | 606/151 |
| 2006/0079911 A1* | 4/2006 | Muramatsu et al. | 606/139 |
| 2006/0122647 A1 | 6/2006 | Callaghan et al. | 606/213 |
| 2007/0060895 A1 | 3/2007 | Sibbitt, Jr. et al. | 604/215 |
| 2007/0203506 A1 | 8/2007 | Sibbitt, Jr. et al. | 606/139 |
| 2009/0254119 A1* | 10/2009 | Sibbitt et al. | 606/213 |

FOREIGN PATENT DOCUMENTS

WO   WO 2005/027753 A1   3/2005 ............. A61B 17/00

* cited by examiner

*Primary Examiner* — Melanie Tyson
(74) *Attorney, Agent, or Firm* — Brinks Gilson & Lione

(57) ABSTRACT

A device for closure of an opening formed through a wall of a body vessel of a patient is provided, as well as an introducer system for delivery of the closure device. Various embodiments include the closure device having hook members configured to engage the tissue interior of the body vessel wall, hook members configured to engage interstitial tissue adjacent to the body vessel, a plug member to contact sealably the opening from inside the body vessel, and combinations thereof. A retraction member is removably attached to the each of the embodiments to permit manipulation of the device. Remodelable material may be included with each of the embodiments to promote quicker healing. The introducer includes a sheath that is insertable through the opening and a pusher disposed within the lumen of the sheath and movable within the sheath lumen to deploy the device.

16 Claims, 11 Drawing Sheets

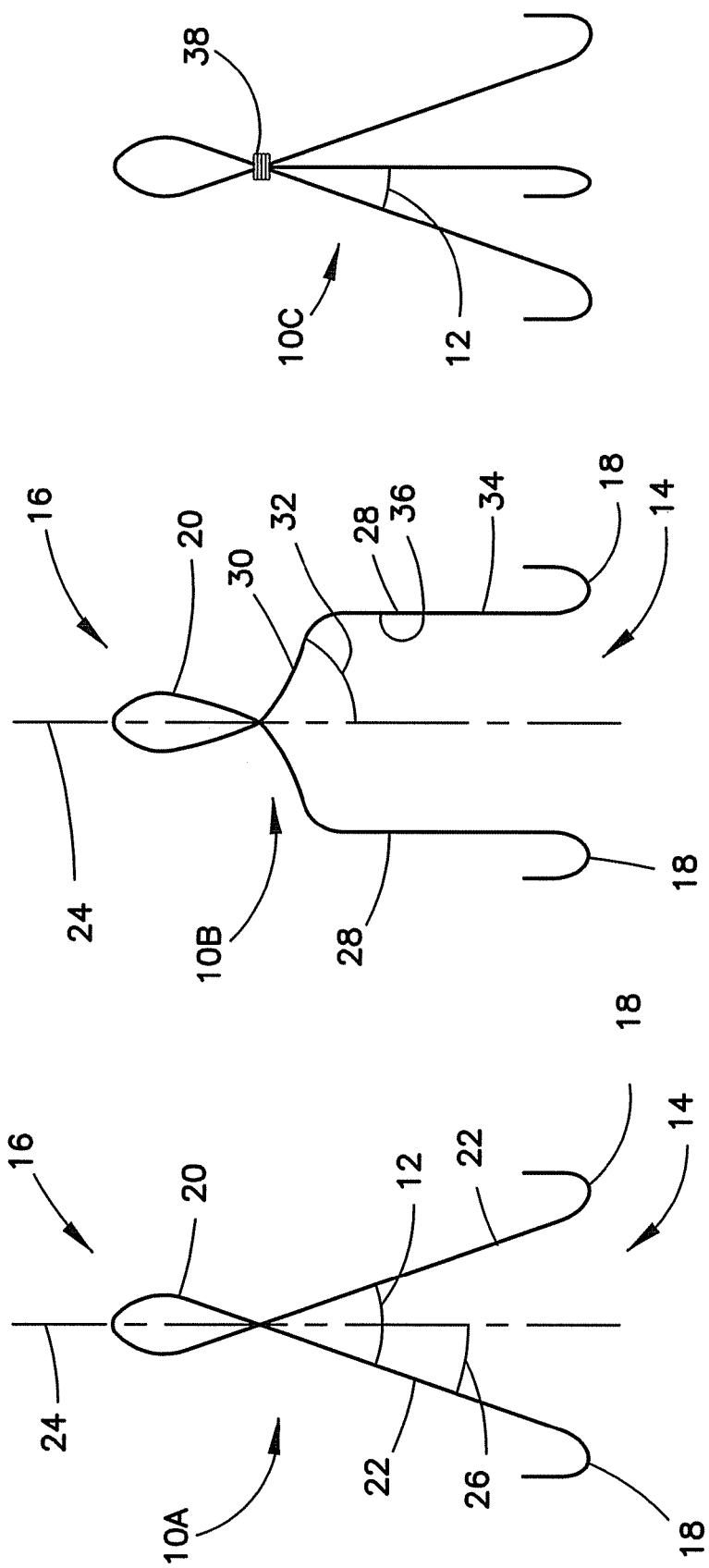

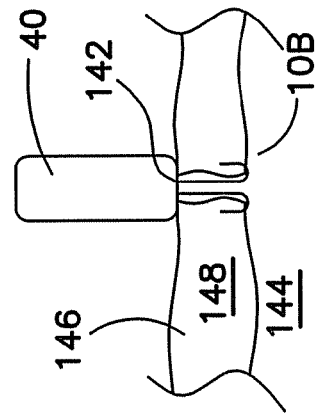
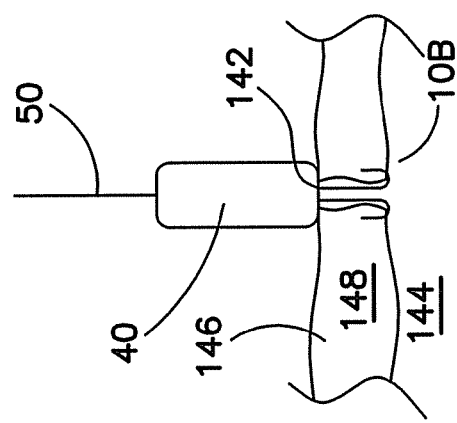
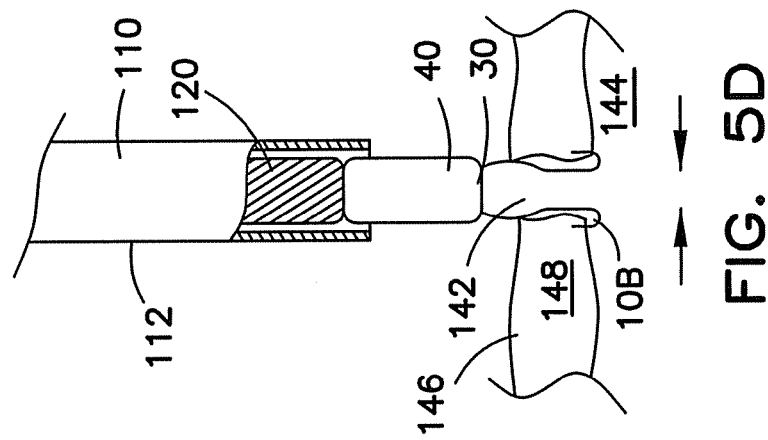

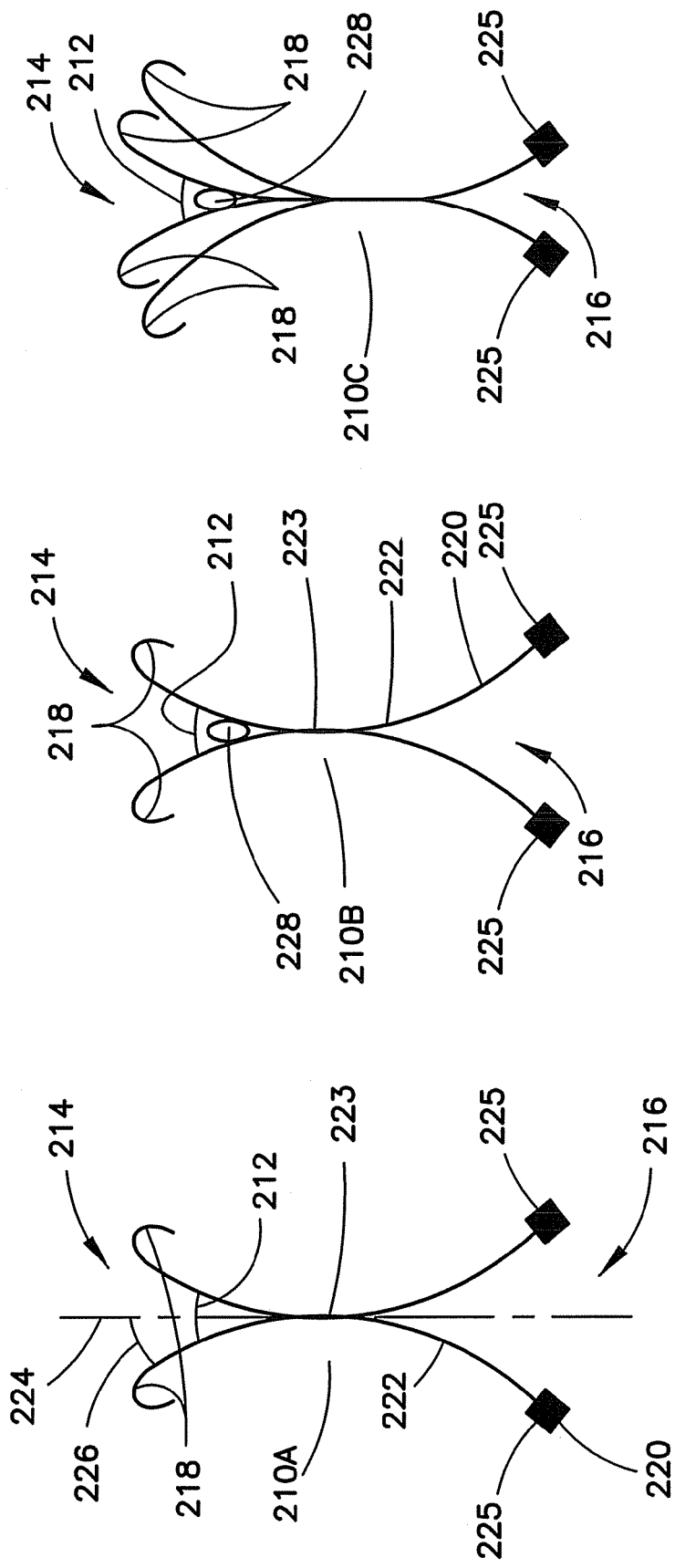

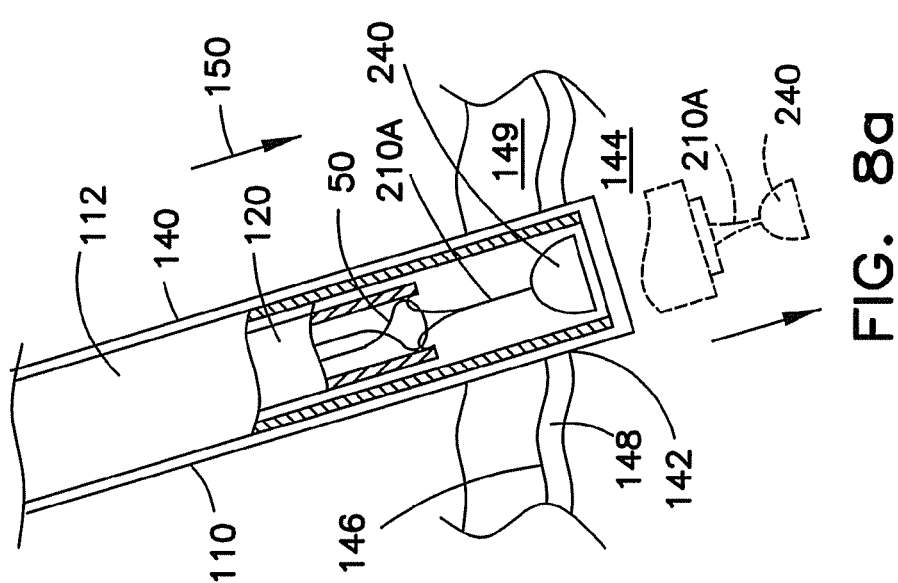
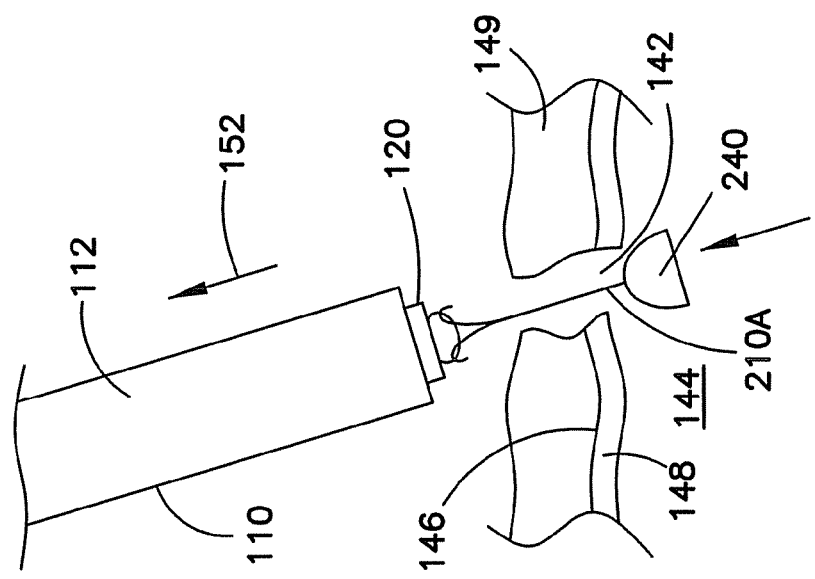
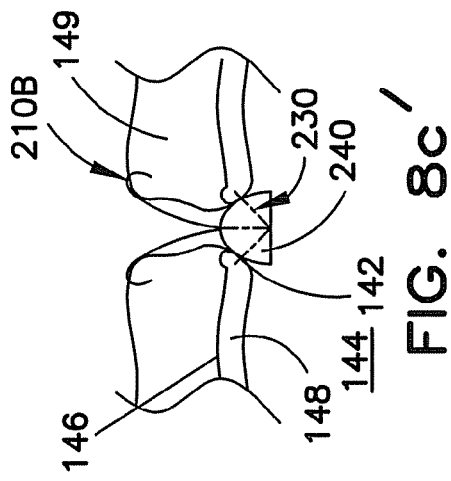
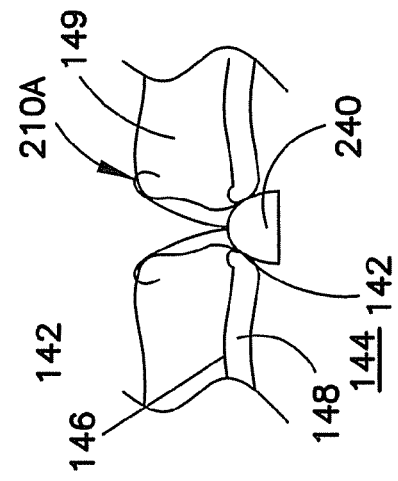

VASCULAR CLOSURE DEVICE

BACKGROUND OF THE INVENTION

1. Technical Field

The present invention relates to a device for closing an opening formed in the wall of a body vessel while carrying out a medical procedure. More particularly, the invention relates to a vascular closure device for closing an opening during deployment of a medical interventional device into the vascular system.

2. Background Information

There are many medical procedures in which a tube, catheter, and/or wire is temporarily inserted into or out of a blood vessel. For example, the Seldinger technique is performed by inserting a hollow needle through a patient's skin and muscle tissue into the vascular system. It is preferable that the needle is passed through the entire vessel, and then pulled back at a steeper angle until blood from the blood vessel flashes in the needle but not all the way out. A guide wire is then passed through the lumen of the needle into the blood vessel. The needle is removed and an introducer sheath is advanced over the guide wire into the vessel. A catheter typically is passed through the lumen of the introducer sheath and advanced over the guide wire into position for a medical procedure, such as angiography, angioplasty, plaque removal, and infusion of a therapeutic agent. As a result, the introducer sheath can facilitate insertion of various devices into the vessel while minimizing trauma to the vessel wall and minimizing blood loss during a procedure. Upon completion of the medical procedure, the catheter and introducer sheath are removed, leaving a puncture vascular access site or opening.

The vascular access site is usually sutured or closed manually by providing pressure with a pressure bandage, compressive weight or clamp device until clotting and wound sealing occurs. The manual pressure method, however, can take half an hour or more and can require the patient to remain immobilized for at least that period of time and be kept in the hospital for observation. Rate of post-puncture hemorrhage can be high leading to considerable complications. There may also be a possibility for clots at puncture site to be dislodged.

Sutures may have procedure variability, but still require time to close the vessel. Sutures typically close the vascular access site by using a "purse-string" suture, in which a single thread is stitched to surround the access site and then pulled tight (like a purse-string) to close the access site. Performing this suture requires skill and practice to capture the suture, withdraw the suture, tie the knot, and cut the suture. It also may be difficult to perform the suturing in a key-hole procedure or in other types of surgery where there is limited access to the wound site. A nidus for thrombus or instravascular mural hyperplasia with later spontaneous and catastrophic closure of the vessel is known to occur because the suture remains intravascularly on the endothelial surface.

It would be desirable to provide an improved closure device, an introducer system, and methods of use therewith, for closing an opening formed in the wall of a body vessel while carrying out a medical procedure that do not suffer from the drawbacks of the conventional approaches.

BRIEF SUMMARY

A device for closure of an opening formed through a wall of a body vessel of a patient, as well as an introducer system for delivery of the closure device and methods of use therewith, are provided. In a first embodiment, the closure device includes hook members configured to engage the tissue interior of the body vessel wall. In a second embodiment, the closure device includes hook members configured to engage interstitial tissue adjacent to the body vessel and a plug member to contact sealably the opening from inside the body vessel.

The anchor body of the closure device can be dimensioned such that the distal end is insertable through the opening to an interior space of the body vessel while the other end is external of the body vessel. The proximal end or the distal end of the anchor body can include at least one portion suitable for engagement with tissue at an exterior or interior of the body vessel to inhibit movement of the anchor body. The closure devices have hook-like extensions that grab tissue of the body vessel wall surrounding the opening. The hook-like extensions are designed to be flexible for manipulation in tissue and delivery, and yet rigid enough when extended to push the tissue engagement structures against the vessel wall. Once closure has been completed, the closure device may be removed or may be left in the body to be bioabsorbed. The closure device may also be coated with a suitable therapeutic agent to promote faster healing.

In a first embodiment, the closure device includes an anchor body having a first end and a second end. The first end can include a plurality of hook members configured to engage tissue of the body vessel. The second end can be configured as an eyelet. The anchor body can be formed of a continuous wire and can be movable between a contracted configuration and an extended configuration. The anchor body can be contractible to fit within the opening, and in the extended configuration the hook members of the anchor body can be displaced outward to a cross-sectional area greater than the cross-sectional area of the opening. The closure device also includes a tubular member having a first end and a second end and a lumen extending therethrough. The lumen can be sized to receive the anchor body in the contracted configuration. The tubular member preferably is slidably engageable with a portion of the anchor body to urge the anchor body to move from the extended configuration to the contracted configuration. The closure device also includes a retraction member disposed within the lumen of the tubular member and removably attached to the eyelet of the anchor body. The retraction member is retractable within the lumen of the tubular member to bring the distal end of the tubular member closer to the first end of the anchor body.

In one variation of the first embodiment, the hook members of anchor body in the extended configuration are disposed about a central axis at an acute angle. In another variation, the hook members of anchor body in the extended configuration includes a first portion disposed about a central axis at an angle about substantially perpendicular thereto, a second portion disposed parallel to the central axis, and a bend interconnecting the first and second portions. Yet, in another variation, the tubular member includes remodelable material attached to the distal end thereof, where the remodelable material is contactable with the opening. In another variation, the remodelable material includes a lumen having a smaller cross-sectional area than the opening and sized to receive the second end of the anchor body. In another variation, the tubular member has a length sized to receive a portion of the anchor body that is external to the body vessel wall. Yet, in another variation, the tubular member is adapted to be positioned external to the body vessel wall. In another variation, the retraction member is lockable to permit manipulation of the anchor body.

A method of closing an opening formed through a wall of a body vessel of a patient with one example of the first embodiment of the closure device is provided below. After inserting the first end of the anchor body through the opening, the anchor body can be moved into the extended configuration in the interior space of the body vessel. The retraction member can be withdrawn such that the hook members engage the body vessel wall. The tubular member can be advanced over a proximal portion of the anchor body to reduce spacing between the hook members and to capture the body vessel wall between the tubular member distal end and the hook members.

In a second embodiment, the closure device includes an anchor body having a first end and a second end. The first end can include a plurality of hook members configured to engage interstitial tissue adjacent to the body vessel to inhibit movement of the anchor body. The anchor body can be movable between a contracted configuration and an extended configuration. In the contracted configuration the anchor body may be sized to fit within a channel through the interstitial tissue, and in the extended configuration the hook members of the anchor body can be displaced outward to a cross-sectional area greater than the cross-sectional area of the opening. The closure device also includes a plug member attached to the anchor body second end. The plug member can be sized to at least substantially fill the opening. The closure device also includes a retraction member removably attached to a portion of the anchor body. The retraction member is retractable to bring the plug member in sealably contact with the opening.

In one variation of the second embodiment, the hook members of anchor body in the extended configuration are disposed about a central axis at an acute angle. In another variation, suitable tension of the retraction member brings the hook members inward to lie in immediate contiguous proximity to one another, and removal of the tension permits the hook members to move outward away from one another to the extended configuration. Yet, in another variation, the plug member comprises a remodelable material.

In another aspect, the closure device includes an anchor body having a first end and a second end, each having hooks and/or barbs. The first end can include a plurality of hook members and/or barbs configured to engage interstitial tissue adjacent to the body vessel to inhibit movement of the anchor body, while the second end can include hooks and/or barbs configured to engage the area surrounding the opening of the body vessel. The anchor body can be movable between a contracted configuration and an extended configuration. In the contracted configuration the anchor body may be sized to fit within a channel through the interstitial tissue, and in the extended configuration the hook members of the anchor body can be displaced outward to a cross-sectional area greater than the cross-sectional area of the opening. The closure device also includes a plug member attached to the anchor body between the first and second ends. The plug member can be sized to substantially fill the opening of the body vessel and a portion of the channel through the interstitial tissue. The closure device also includes a retraction member removably attached to a portion of the anchor body. The retraction member is retractable to bring the plug member in sealably contact with the opening.

A method of closing an opening formed through a wall of a body vessel of a patient with one example of the second embodiment of the closure device is provided below. The second end of the anchor body can be inserted through the opening such that the plug member is disposed within an interior space of the body vessel. The retraction member can be withdrawn such that the plug member sealably contacts the opening. The anchor body can be moved into the extended configuration such that the hook members engage with interstitial tissue adjacent to the body vessel to inhibit movement of the anchor body and to maintain sealably contact between the plug member and the opening.

An introducer system for closure of an opening formed through a wall of a body vessel of a patient is also provided. The system can include a sheath having a proximal end and a distal end, and has a lumen extending therethrough. The distal portion of the sheath is insertable through the opening. A pusher is disposed within the lumen of the sheath and movable within the sheath lumen. The pusher has a proximal end and a distal end and a lumen extending therethrough. One of the embodiments of the closure device is loaded into the introducer system. Preferably, the introducer system is introduced to the body vessel via a sheath already positioned through the opening from a previous procedure.

BRIEF DESCRIPTION OF THE DRAWINGS

FIGS. 1a-1c are side views of variations of a first embodiment of closure devices.

FIGS. 5a-5f are side views partially in cross-section depicting one method of using the introducer of FIG. 4 and the closure device of FIG. 1b.

FIGS. 6a-6c are side views of variations of a second embodiment of closure devices.

FIG. 7a is a side view of a plug member attached to the vascular closure device of FIG. 6a.

FIGS. 8a-8c are side views partially in cross-section depicting one method of using the introducer of FIG. 4 and the closure device of FIG. 7a.

FIG. 8c' is a side view depicting the closure device of FIG. 7b delivered to an opening of a body vessel.

DESCRIPTION OF PREFERRED EMBODIMENTS

Figure 2B:
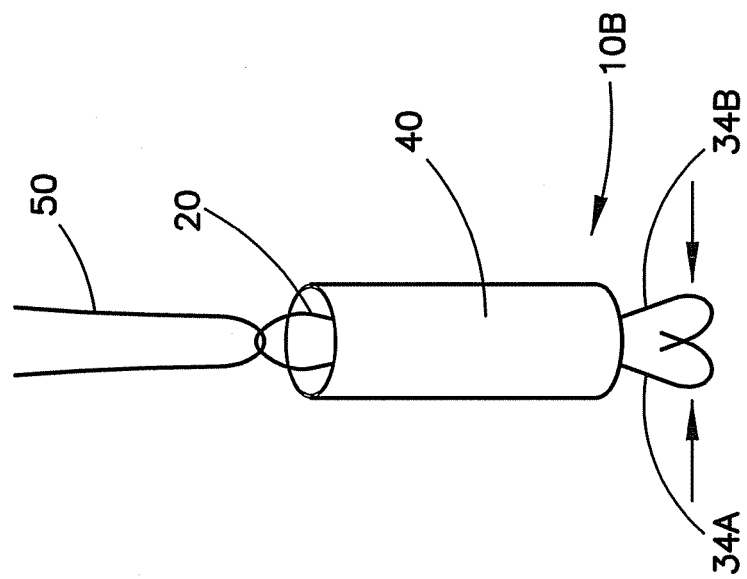
FIGS. 2a-2b are side views of a tubular member sliding over the closure device of FIG. 1b.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive device, as well as the axial ends of various component features. The term "proximal" is used in its conventional sense to refer to the end of the device (or component thereof) that is closest to the operator during use. The term "distal" is used in its conventional sense to refer to the end of the device (or component thereof) that is initially inserted into the patient, or that is closest to the patient during use.

Closure devices and introducer systems for deploying the closure devices are provided. The closure device generally includes an anchor body having a proximal end and a distal end. The anchor body can be dimensioned such that the distal end is insertable through the opening to an interior space of the body vessel while the other end is external of the body vessel. The proximal end or the distal end of the anchor body can include at least one portion suitable for engagement with tissue at an exterior or interior of the body vessel to inhibit movement of the anchor body. The closure devices have hook-like extensions that grab tissue of the body vessel wall surrounding the opening. The hook-like extensions are designed to be flexible for manipulation in tissue and delivery, and yet rigid enough when extended to push the tissue engagement structures against the vessel wall.

FIGS. 1a-1c afford variations of a first embodiment of a closure device to be applied with an internal anchor. In the first embodiment, the closure device grabs the vessel wall from inside the body vessel with hook-like extensions. The hook-like extensions are pulled together by sliding a tubular member over the closure device to cause a frictional fit between the closure device and the tubular member. The vessel is then captured between the distal end of the tubular device and the hook-like extensions.

In each of the variations of the first embodiment, the closure device includes a plurality of hook members 12 having a first end 14 and a second end 16 to form the anchor body. The first end 14 is configured to engage the tissue surrounding the opening in the body vessel. The second end is configured to receive a retraction member as described below.

In FIG. 1a, the closure device 10A includes the hook members 12 that are shown as one continuous wire formed with hooks 18 at the first end 14, an eyelet 20 at the second end 16 and a substantially straight member 22 therebetween. The straight member 22 can be angled from a central axis 24 with an angle 26 suitable to permit movement away from the central axis 24 to position the hooks 18 to contact the surrounding area of the opening. In FIG. 1b, the closure device 10B includes the hook members 12 that are shown as one continuous wire formed with hooks 18 at the first end 14, an eyelet 20 at the second end 16 and a bent member 28 therebetween. The bent member 28 can have a first portion 30 that can be angled from a central axis 24 with an angle 32 suitable to permit movement away from the central axis 24 to position the hooks 18 to contact the surrounding area of the opening. The bent member 28 can also have a second portion 34 that can be substantially parallel to the central axis 24, where the first and second portions 30, 34 are joined by a bend 36. In FIG. 1c, the closure device 10C includes the hook members 12, similarly situated as shown in FIG. 1a, that are shown as three components joined at an attachment point 38 with suitable means. The hook members are configured to move between a contracted configuration where the hook members are placed to lie in immediate contiguous proximity to one another and an extended position where the hook members are moved outwardly away from one another. The hook members may be biased toward the extended configuration.

The closure device can also include a tubular member 40. For example, in FIGS. 2a-2b, the tubular member 40 is shown with the closure device 10B. The tubular member 40 has a proximal end 42 and a distal end 44 and a lumen 46 extending therethrough. The lumen 46 of the tubular member 40 is sized to receive slidably the closure device 10B in the contracted configuration. Preferably, the length of the tubular member 40 is dimensioned to at least receive the portion of the closure device that is external to the body vessel when deployed.

Figure 2A:
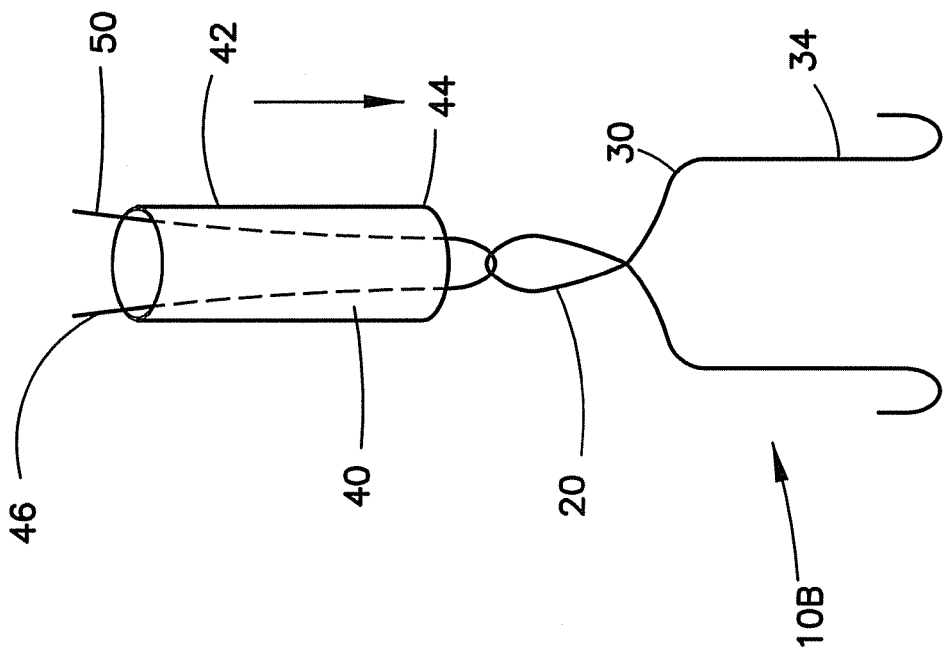

In FIG. 2a, a retraction member 50 is shown looping through the eyelet 20 of the closure device 10B, with the tubular member 40 disposed around the retraction member 50 and proximal to the closure device 10B, in the extended configuration. FIG. 2b illustrates the tubular member 40 sliding over the eyelet 20 of the closure device 10B to contact the first portion 30. As the tubular member 40 continues to move in the distal direction, the sliding contact between the tubular member 40 and the first portion urges the second portion 34A of one hook member to converge inward and cross the second portion 34B of another. In one example, the closure device is configured so that when the tubular member urges the hook members to converge, the hooks move inward along a single direction. This can pull the edges of the opening together to abut one another for healing. The retraction member 50 may be maintained in tension as the tubular member 40 is moved. In one embodiment, the tubular member and the closure device comprise a biodegradable material.

Figure 3C:
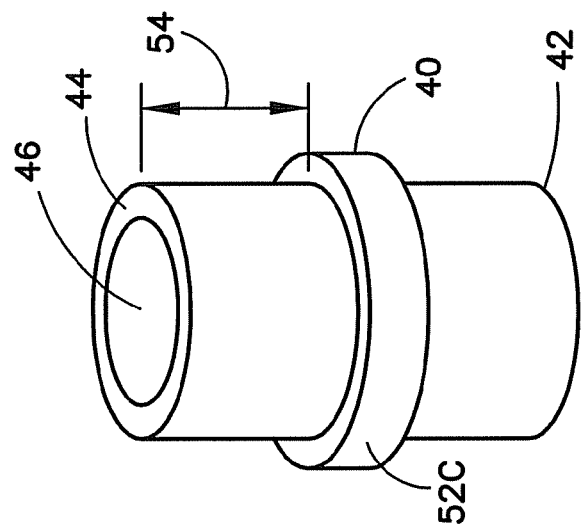
FIGS. 3a-3c are perspective views of various embodiments of tubular members with remodelable material.
Figure 3B:
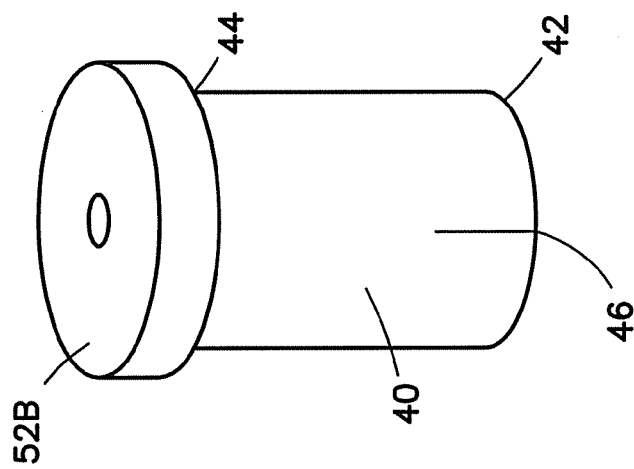
Figure 3A:
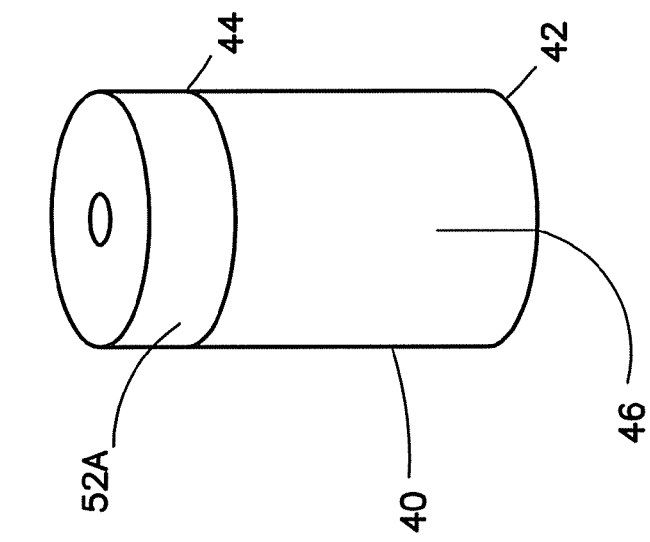

FIGS. 3a-3c illustrate various embodiments of the tubular member 40 with a portion of remodelable material, as further described herein. Remodelable material is capable of remodeling or promoting cell growth and/or promoting regrowth and healing of damaged or diseased tissue structures, and includes extra cellular material (ECM), small intestine submucosa (SIS), or other described below. In FIG. 3a, the remodelable material 52A can be sized to match the outer and inner diameters of the tubular member 40. The remodelable material 52A can attach to the distal end 44 of the tubular member 40 via various methods known in the art. Optionally, the remodelable material 52A may include a lumen 53 having a smaller cross-sectional area than the opening and/or the lumen of the tubular member and being sized to receive the second end of the closure device upon movement of the tubular member 40. In another embodiment shown in FIG. 3b, the remodelable material 52B has a larger diameter than the tubular member 40 and an inner diameter of the lumen 53 equal to or less than the inner diameter of the tubular member 40. The remodelable material 52B attaches the distal end 44 of the tubular member 40. Yet, in another embodiment shown in FIG. 3c, the remodelable material 52C has a larger diameter than the tubular member 40 and an inner diameter equal to the outer diameter of the tubular member 40. The remodelable material 52B slidably attaches to the exterior surface of the tubular member at a predetermined distance 5 from the distal end 44 of the tubular member 40.

Figure 4:
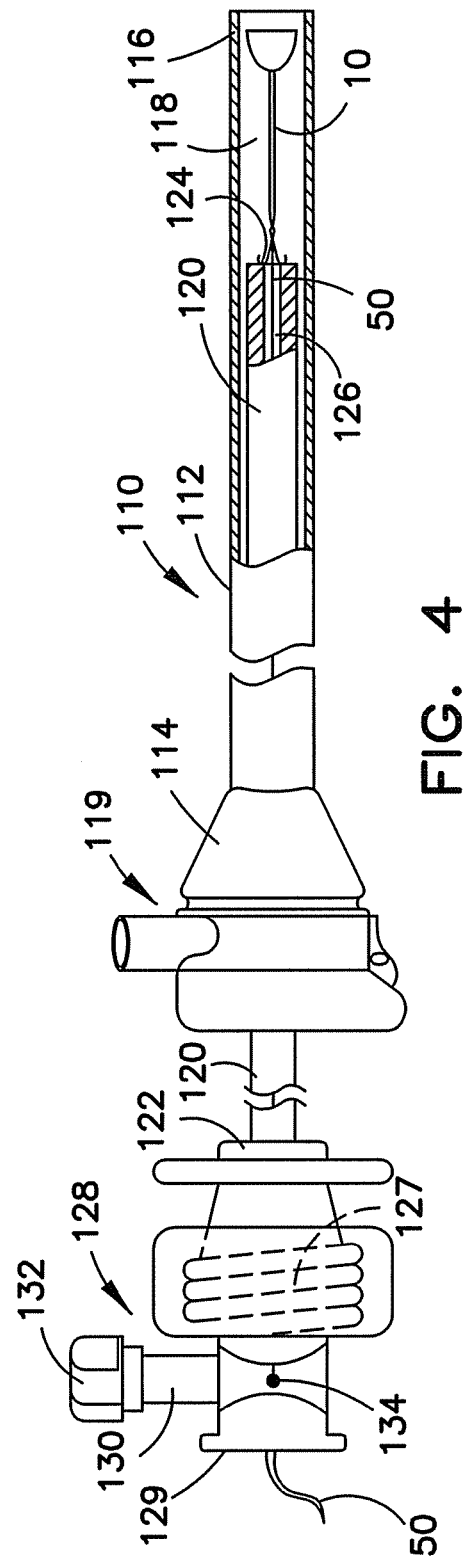
FIG. 4 is a side view partially in cross-section of an exemplary introducer system.

FIG. 4 illustrates an exemplary embodiment of an introducer 110 for delivery of a closure device. The introducer 110 includes an outer sheath 112 having a proximal end 114 and a distal end 116 and a lumen 118 extending through the body of the outer sheath 112. The outer sheath 112 can be a tubular body being sized to be inserted through the opening of the body vessel or through the lumen of a sheath left from the previous medical procedure. The proximal end 114 of the outer sheath 112 can be disposed within a hub assembly 119. The hub assembly 119 can have a strain relief, a fluid port, and a valve. The closure device 10 can be loaded into the distal portion of the lumen 118 of the outer sheath 112.

The introducer 110 further includes a pusher 120 disposed within the lumen 118 of the outer sheath 112 and movable within the sheath lumen 118. The pusher 120 has a proximal end 122 and a distal end 124 and a lumen 126 extending through the body of the pusher 120. The pusher 120 can be a tubular body sized to be inserted through the lumen 118 of the outer sheath 112 and can slidably engage with the luminal surface of the outer sheath 112. The proximal end 122 of the pusher 120 can extend past the proximal end 114 of the outer sheath 112, and can extend through the valve section of the hub assembly 119. The proximal end 122 of the pusher 120 can be connected to a pusher handle 128. The pusher 120 is configured to move between a fully retracted position distally in the lumen 118 of the outer sheath 112, and a fully extended position proximally away from the outer sheath 112.

The pusher handle 128 has a lumen 127 therethrough to permit fluid communication with the lumen 126 of the pusher 120. The lumen 127 can extend through the axial end 129 of the pusher handle 128. The pusher handle 128 can have a portion that can be detached to permit easier loading of the retraction member 50. Another portion of the pusher handle 128 includes a locking mechanism to lock or affix the retraction member 50 at a specific location. In one example shown in FIG. 4, the locking mechanism is a manual stop cock valve 130 having an external lever 132 and a port 134 through the body of the stop cock valve 130. The external lever 132 can be rotated to a first position, "open," that aligns the port in fluid communication with the lumen 126 of the pusher 120 and to a second position, "closed," that blocks any fluid communication with the lumen 126 of the pusher 120. The lumen 126 of the pusher 116 and the port 134 of the stop cock valve 130 can be sized to receive the retraction member 50.

Other examples of the locking mechanism include a spring-loaded push button. The spring loaded push button includes a button attached to a shaft that has a spring mechanism attached thereto to bias the button toward the outward position or closed position. The shaft includes a port, similar to the port of the stop cock valve. The button can be pressed to a first position, "open," that aligns the port in fluid communication with the lumen of the pusher and to a second position, "closed," that blocks any fluid communication with the lumen of the pusher.

The retraction member 50 can be removably attached to the closure device. In one example shown in FIG. 4, the retraction member 50 loops around the hooks of the closure device and traverses the lumens 126, 127 of the pusher 120 and the pusher handle 128. The portion with the stop cock valve 130 can be detached from the pusher handle 128, and with the stop cock valve 130 in the first position, the ends of the retraction member 50 can be fed through the port 134 of the stop cock valve 130 and be extended past the axial end 129 of the pusher handle 128, as shown in FIG. 4. When the stop cock valve 130 is in the first position, the retraction member 50 is free to move within the introducer 110. When the stop cock valve 130 is in the second position, the retraction member 50 is locked or affixed at a location and prevented from moving within the introducer 110.

Figure 5C:
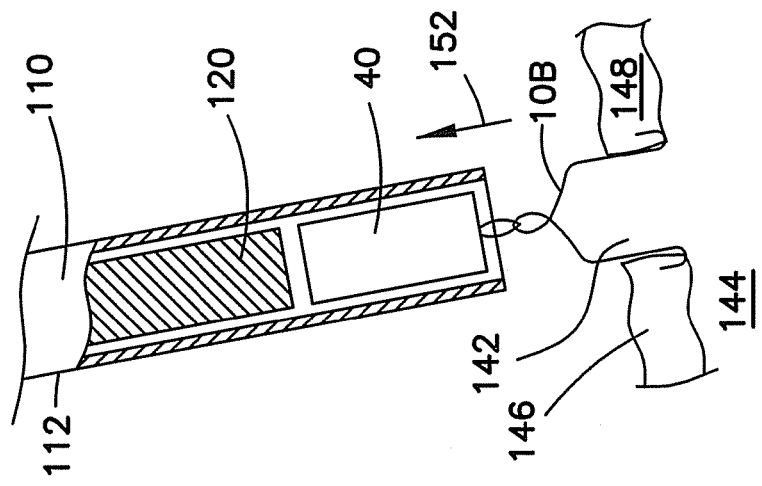
Figure 5B:
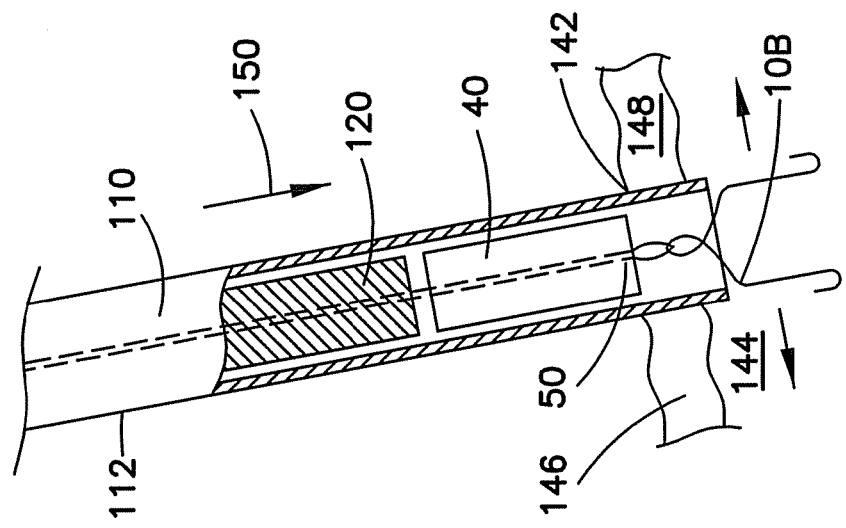
Figure 5A:
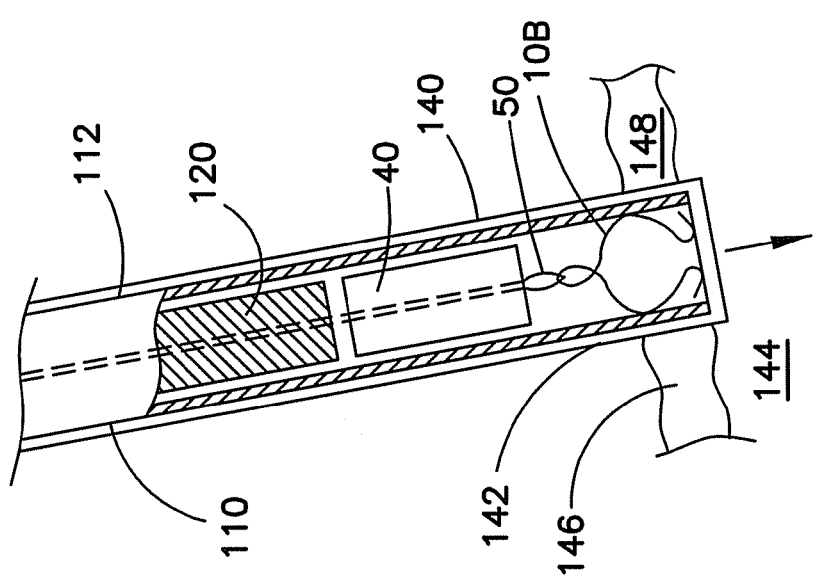

With reference to FIG. 5a, the closure device 10B, as exemplary of the first embodiment of closure devices can be loaded into the introducer 110 by the following method. The pusher 120 can be extended to allow enough space to receive the closure device 10B and/or the tubular member 40. The retraction member 50 can be attached to the closure device 10B through the tubular member 40 and fed and loaded into the introducer 110, as described herein. With the retraction member 50 being free to move, the retraction member 50 can be pulled from a location external to the axial end 129 to draw and urge the tubular member 40 and/or the closure device 10B within the lumen 118 of the outer sheath 112. The tubular member 40 is sized to fit within the lumen of the introducer. Once in a suitable position, the retraction member 50 can be put in the locked position.

FIGS. 5a-5f depict the use of the introducer 110 with a closure device, for example the closure device 10B as described above. The introducer 110 can be introduced to a body vessel 146 in order for a distal portion of the introducer 110 to access an interior space 144 of the body vessel 146 through an opening 142. The opening 142 is usually created through the wall 148 of the body vessel 146 after an invasive procedure requiring a sheath 140 to be inserted therethrough to allow other medical devices to gain access to the interior space 144 of the body vessel 146. It is to be understood that the present invention can be used with any opening regardless how the opening was created.

In FIG. 5a, the introducer 110 has a loaded closure device 10B with the tubular member 40 disposed proximal thereto. The distal end of the pusher 120 is shown to be adjacent to the tubular member 40, with the pusher 120 in an extended position. Preferably, before removal of the sheath 140, the introducer 110 is inserted through the lumen of the sheath 140. This can provide a smoother insertion of the introducer 110 through the wall 148 and into the body vessel 146. The retraction member 50 can be put into a locked position before insertion. The introducer 110 is preferably placed in a position where the distal portion of the introducer is slightly in the interior space 144 of the body vessel 146. After placement, the sheath 140 may be removed slightly away from the body vessel to allow the opening of the body vessel wall to converge slightly about the introducer.

According to FIG. 5b, with the retraction member 50 still in the locked position, the pusher 120 can be moved in the distal direction, represented by arrow 150, relative to the introducer 110. The pusher 120 can engage with and urge the tubular member 40 to move in the distal direction, which causes the closure device 10B to exit the distal end of the outer sheath 112 and enter into the interior space 144 of the body vessel 146. With a proximal portion of the closure device 10B still within the introducer 110, the hooks of the closure device 10B are moved to the extended configuration when the closure device exits the introducer. The closure device 10B is configured to move outward such that the hooks are positioned at wall tissue beyond or surrounding the opening 142. In FIG. 5c, the introducer 110 can then be pulled in the proximal direction, represented by arrow 152, to allow the hooks of the closure device 10B to engage and penetrate the interior of the body vessel wall 148. The hooks may penetrate a portion of the body vessel wall, but can also penetrate substantially the entire body vessel wall. In some examples, the hooks penetrate the entire body vessel wall and extend beyond the body vessel wall. Preferably, the introducer 110 is placed in a position adjacent the opening 142 but outside the body vessel 146.

In FIG. 5d, with the retraction member 50 in freed position, the pusher 120 can be moved in the distal direction, represented by arrow 150, relative to the introducer 110 while maintaining the string member fixed. The pusher 120 can engage with and urge the tubular member 40 to move in the distal direction to a position outside the introducer 110. The tubular member 40 slides over the closure device 10B to contact therewith, urging the closure device 10B to converge inward. The tubular member 40 can be moved toward the penetrated hooks until its distal end 44 contacts the body vessel 146. This reduces the spacing between the hooks of the closure device 10B and captures the body vessel wall 148 between the distal end 44 of tubular member 40 and the hooks of the closure device 10B. The distal end 44 of the tubular member 40 may have remodelable material, as described herein. Since the retraction member 50 is in the unlocked position, the portion of the retraction member 50 external to the body can be pulled, while maintaining the introducer and the pusher in a fixed position, to cinch and bring closer the closure device 10B toward the tubular member 40. As shown in FIG. 5e, with the retraction member 50 put into the free position, the introducer 110 may be removed from the body. The closure device 10B and the tubular member 40 are left in the body. The retraction member may then removed, as shown in FIG. 5f.

During closure of the opening in the body vessel with the closure device of the first embodiment, a portion of the edge of the opening is moved inward to abut another portion to close the opening in the body vessel. Since the closure device brings the opening edges together, there can be true blood vessel healing with little endothelial disruption, reducing the chances of thrombosis or intimal hyperplasia. The closure device can be supplied in different diameters (e.g., French sizes) to accommodate different sizes of catheters and different sizes of the opening. When the edges of the opening are brought together, blood flow therethrough is at least substantially inhibited, and the closure can be completed. By holding the closure device in place until clotting occurs, closure can occur through the self-healing process or as a result of the clotting. Once closure has been completed, the closure device may be removed or may be left in the body to be bioabsorbed.

FIGS. 6a-6c afford variations of a second embodiment of a closure device to be applied with an external anchor. In the second embodiment, the closure device grabs interstitial tissue externally adjacent the vessel wall with hook-like extensions, while a plug-like member closes and seals the opening from the inside of the body vessel. The hook-like extensions are releasable to secure the plug-like member in place. In each of the variations of the second embodiment, the closure device includes an anchor body such as a plurality of hook members 212 having a first end 214 and a second end 216. The first end 214 is configured to engage the interstitial tissue externally adjacent the opening in the body vessel to inhibit movement of the anchor body. Such interstitial tissue surrounds the body vessel and can include connective tissue, fatty tissue, muscular tissue or the like. The second end 216 is configured to receive a plug like structure. A portion of the closure device is configured to receive a retraction member as described below.

In FIG. 6a, the anchor body of the closure device 210A includes the hook members 212 that are shown as discrete wires formed with hooks 218 at the first end 214, a pointed end 220 at the second end 216 and a middle region 222 therebetween. The middle region 222 of the hook members 212 can each be attached at an attachment point 223 by wrapping the hook members 212 around each other, welding, soldering, or the like. The pointed end 222 can include additional material to form a tabbed end 225 for better engagement with a plug-like member. The portion of the middle region 222 that is near the first end can be angled from a central axis 224 with an angle 226 suitable to permit movement away from the central axis 224 to position the hooks 218 to contact the surrounding area of the opening. In FIG. 6b, the anchor body of the closure device 210B includes a similar structure as the closure device 210A except an eyelet 228 can be located between the hooks 218 and the attachment point 223. The eyelet 228 can permit better securement between the retraction member 50 and the closure device. For example, the eyelet 228 allows the retraction member 50 to be secured to the closure device to keep an upward force on the plug member while the hooks are deployed. In FIG. 6c, the anchor body of the closure device 210C includes four hook members 212 attached at the attachment point 223 and shown with an eyelet 228. Although the closure devices of the second embodiment are shown formed from discrete wires, it is understood that these closure devices could be formed from one continuous wire similar to other closure devices described above.

The closure device can also include a plug member 240 at the second end 216. The plug member 240 may consist of a remodelable material, as described below, or any biodegradable materials, such as biodegradable polymers like PLA, PLGA, or the like, as described below. The plug member 240 is sized to at least substantially fill and seal the opening upon movement of the closure device. The plug member 40 can be a variety of shapes, including but not limited to: hemispherical, spherical, conical, frustum conical, or the like. The second end 216 of the hook members can be embedded or molded within the center of the plug member 240. The second end 216 may have a tab 225 and the plug member 240 is fixedly attached to the tab 225 of the second end 216. One method of making the closure device 210 is to attach two or more hook members as described above with each second end lying adjacent to one another. The plug member can then slide over the second end to allow the second ends to penetrate through the plug member. With the second ends completely through the plug member, the second ends can be bent outwardly to a suitable distance and angle. The plug member can then slide back toward the second ends to contact therewith, and a suitable adhesive, if needed, can be applied to secure the plug member to the second ends of the anchor body.

Figure 7A:
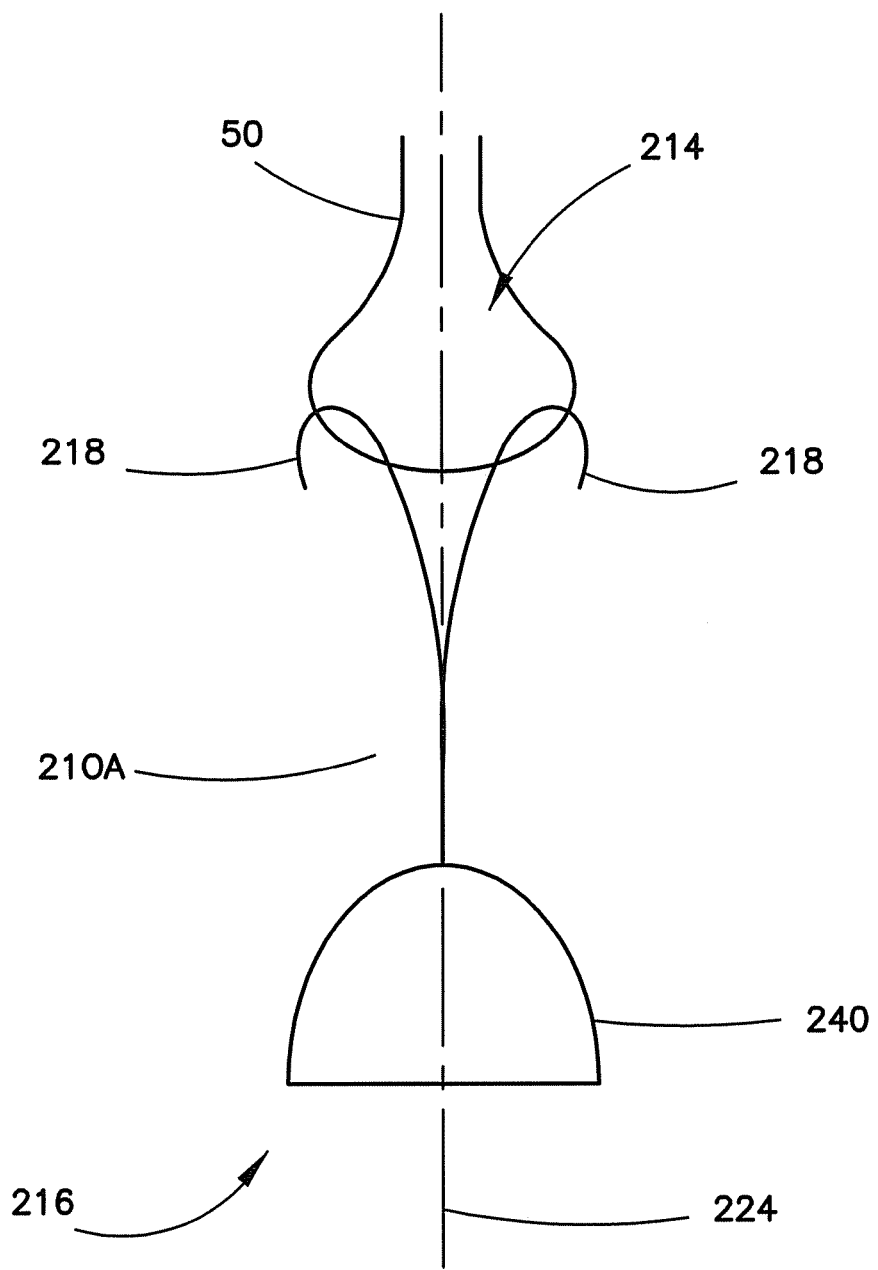

In FIG. 7a, the plug member 240 is shown with the anchor body of the closure device 210A. In FIG. 7a, a retraction member 250 is shown looping through the hooks 218 of the closure device 210A. Tension on the retraction member 250 urges the hooks 218 to converge inward toward the central axis 224. The release of the tension of the retraction member 250 permits the hooks 218 to move outward away from the central axis 224.

Figure 7B:
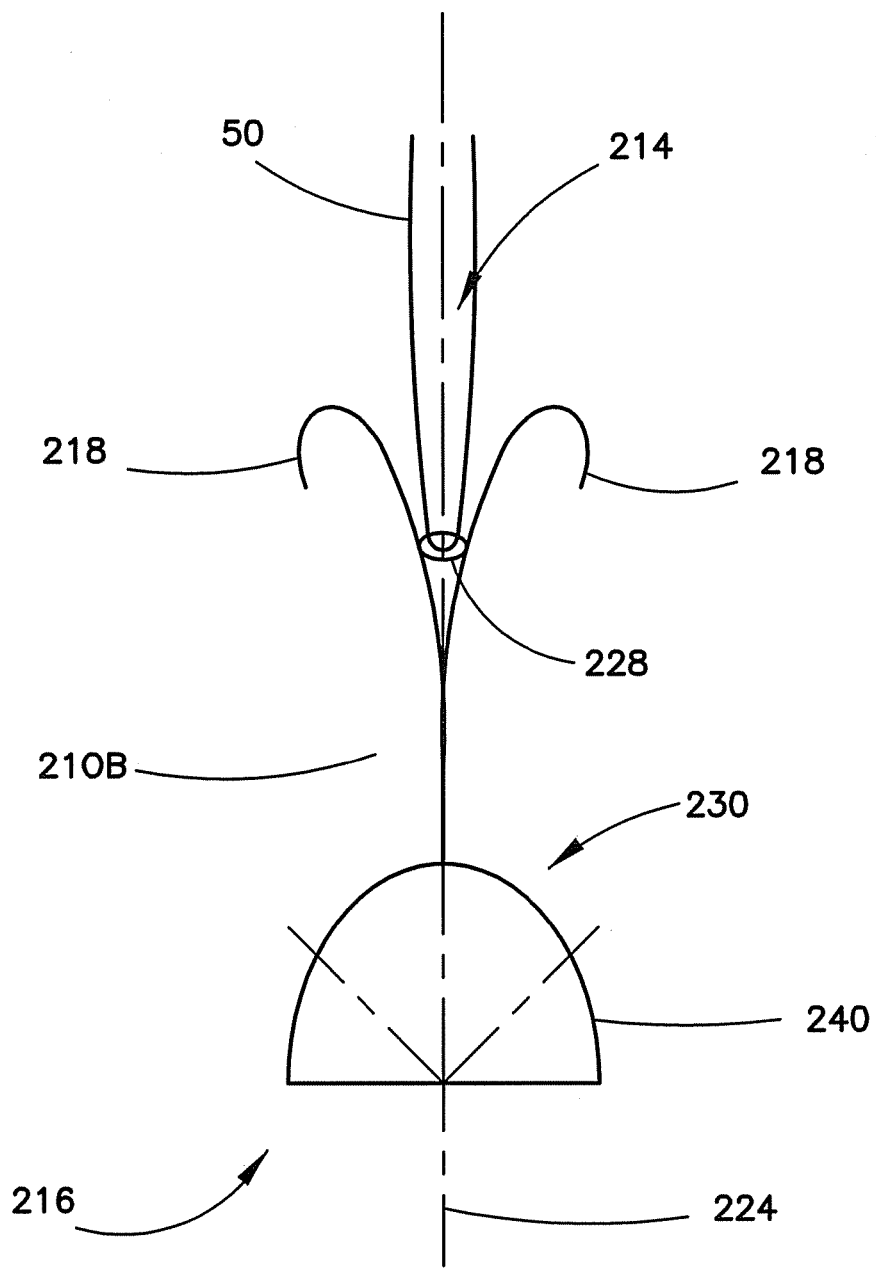
FIG. 7b is a side view of a plug member attached to the vascular closure device of FIG. 6b.

In FIG. 7b, the plug member 240 is shown with the anchor body of the closure device 210B with an additional modification of barbs 230 penetrating outward away from the central axis 224. The barbs 230 are configured to prevent the possibility of the plug member from being pulled through the opening the vessel wall. It is preferable that the barbs 230 are also angled toward the first end 214 at a suitable angle. The barbs 230 may also be curved like the hooks 218 shown in FIG. 7b to decrease interaction with the introducer wall which can aid in loading and delivery of the closure device. The barbs can be formed by bending the second ends of the anchor body such that the second end extends outward past the plug member by a suitable length. Additional segments of anchor body material can be attached to the anchor body by suitable means to form additional barbs.

The closure device 210A, as exemplary of the second embodiment of closure devices, can be loaded into the introducer 110, similar to what is shown in FIG. 4, for delivery of the closure device to the opening. The pusher 120 can be extended to allow enough space to load the closure device 210A and the plug member 240. The retraction member 50 can be removably attached to the closure device 210A through the hooks 218 or the eyelet 228 and fed and loaded into the introducer 110, as described herein. With the retraction member 50 in the free position, the retraction member 50 can be pulled to draw and urge the closure device 210A and the plug member 240 within the lumen 118 of the outer sheath 112. Once in a suitable position, the retraction member 50 can be put in the locked position.

FIGS. 8a-8c depict the use of the introducer 110 with a closure device, for example the closure device 210A in FIG. 7a as described above. In FIG. 8a, the introducer 110 has a loaded closure device 210A with the plug member 240 disposed distal thereto. The sheath 140 is shown penetrating through interstitial tissue 149, such as connective tissue, fatty tissue, muscular tissue or the like, exterior to the body vessel 146 with the introducer 110 inserted therethough. The distal end of the pusher 120 is shown to be adjacent to the hooks of the closure device 210A, with the pusher 120 in the retracted position. The distal end of the pusher 120 can be notched to better receive the hooks. The notches may be created by cutting through the wall of the introducer from the distal end and can be sized to receive the width of the material used to make the hook members. The notches can allow farther retraction of the hooks within the lumen of the pusher. Preferably, before removal of the sheath 140, the introducer 110 is inserted through the lumen of the sheath 140. This can provide a smoother insertion of the introducer 110 through the wall 148 and into the body vessel 146. The retraction member 50 is put into the locked position during insertion. The introducer 110 is preferably placed in a position where the distal end of the outer sheath 112 is slightly in the interior space 144 of the body vessel 146. After placement, the sheath 140 may be removed slightly away from the body vessel wall to allow the tissue and the opening of body vessel wall to converge about the introducer.

According to FIG. 8*a*, with the retraction member 50 in the locked position, the pusher 120 can be moved in the distal direction, represented by arrow 150, relative to the introducer 110 to engage with and urge the closure device 210A to move in the distal direction. The plug member 240 of the closure device 210A can be urged to exit the distal end of the outer sheath 112, as shown by the partial figure in dashed lines, to expose the plug member to the interior space of the body vessel. With the hooks of the closure device 210A still within the introducer 110. In FIG. 8*b*, the plug member 240 is positioned within the interior space 144 of the body vessel 146. The entire introducer 110 can then be pulled in the proximal direction, represented by arrow 152, to allow the plug member 240 to sealably engage the opening 142 from within the interior space 144 of the body vessel wall 148. Preferably, the introducer 110 is placed in a position adjacent the opening 142 but outside the body vessel 146.

According to FIG. 8*c*, the retraction member 50 is put into the free position and removed from attachment to the closure device 210A. This removal permits the hooks of the closure device 210A to engage and penetrate the interstitial tissue 149 adjacent the opening 142. As shown in FIG. 8*c*, with the retraction member 50 put into the free position, the introducer 110 can be removed from the body, leaving the closure device 210A in the body. The retraction member 50 can then be removed, as shown in FIG. 8*c*.

FIG. 8*c*' depicts the use of the introducer with a closure device, for example the closure device 210B in FIG. 7*b* as described above, after the closure device is delivered. Upon removal of the sheath of the introducer, the plug member 240 and barbs 230 are exposed to the interior space 144 of the body vessel 146. When the plug member 240 is pulled to sealably contact the opening 142, the barbs 230 can engage the surrounding tissue from inside of the body vessel 240 to help secure the plug member at the opening and prevent the plug member from being pulled completely out. The eyelet 228 of the closure device allows the retraction member to be secured to the closure device in order to keep an upward force on the plug member while the hooks are deployed to engage and penetrate the interstitial tissue adjacent the opening. In this instance, the hooks are deployed by removal of the hooks from the introducer lumen. The retraction member is then removed from securable contact with the closure device.

Figure 9A:
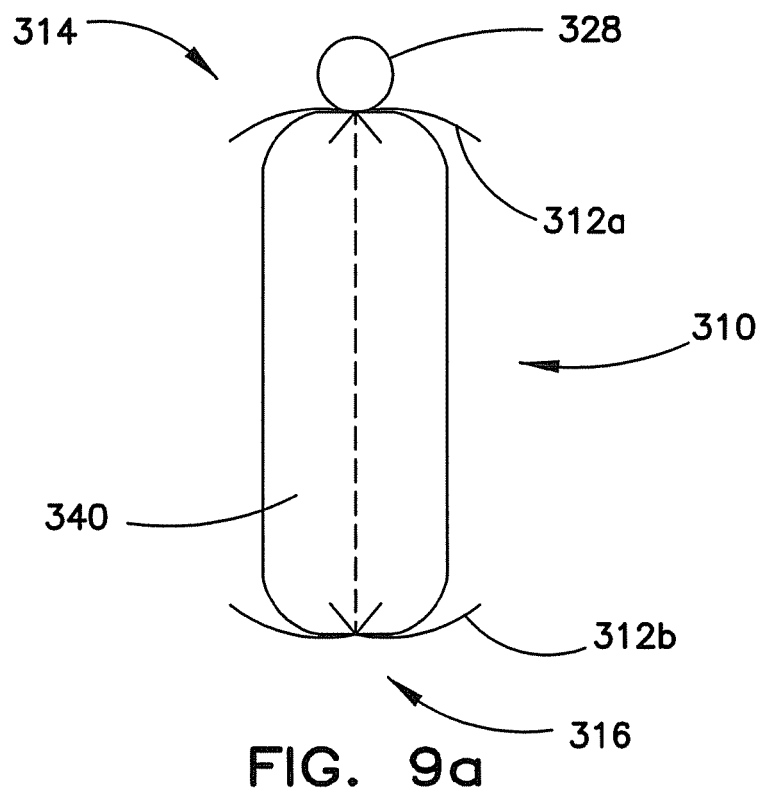
FIG. 9a is a side view of a closure device.

FIG. 9*a* affords a third embodiment of a closure device to be applied with an external and internal anchor. In the third embodiment, the closure device grabs interstitial tissue externally adjacent the vessel wall and grabs the vessel wall from inside the body vessel with hook-like extensions, while a plug-like member between the hook-like extensions closes and seals the opening therebetween. The hook-like extensions are releasable to secure the plug-like member in place.

In the third embodiment, the closure device 310 includes an anchor body similarly constructed as described herein with reference to the first and second embodiments. For example, the closure device 310 has a proximal end 314 and a distal end 316. The proximal end is configured to engage the interstitial tissue externally adjacent the opening in the body vessel to inhibit movement of the anchor body. The distal end is configured to engage tissue surrounding the opening in the body vessel. In one embodiment, the proximal end 314 is similarly constructed as described herein with reference to the first end of the second embodiment of the closure device, while the distal end 314 is similarly constructed as described herein with reference to the first end of the first embodiment. In other examples, barbs or additional hooks, similarly constructed as described herein with reference to the barbs in FIG. 7*b* can be attached to the anchor body of the closure device at the proximal and distal ends to provide additional engageability with the tissue and body vessel. In another example, the anchor body includes an axial member and a plurality of barbs each having one end attached to the anchor body at the proximal and distal ends of the axial member. Preferably, the ends of the barbs are attached at one junction at the proximal and distal ends. In FIG. 9*a*, the hooks and/or barbs 312*a* of the proximal end 314 can be configured to point at an angle toward the distal end 316 to prevent the plug member 340 from moving toward the body vessel, while the hooks and/or barbs 312*b* of the distal end 316 can be configured to point at an angle toward the proximal end 314 to prevent the plug member 340 from moving out of the opening toward the interstitial tissue. A portion of the closure device is configured to receive a retraction member. For example, an eyelet 328 can be located proximal to the proximal end 314 to permit better securement between the retraction member and the closure device.

The closure device 310 includes a plug member 340 between the proximal and distal ends 314, 316. The plug member 340 may consist of remodelable material or any biodegradable material, as described below. The plug member 340 is sized to substantially fill and seal the opening of the body vessel and a portion of the opening through the interstitial tissue. It is preferable that the plug member 340 be cylindrical or tubular, but can be a variety of shapes. In other examples, the plug member can be shaped at the respective ends, such as conical or rounded or the like, as shown in FIG. 9*a*, to allow the hooks and/or barbs 312*a,b* to move to a contracted configuration while being delivered. Then, once delivered, the hooks and/or barbs 312*a,b* can move to the extended configuration. If tubular, the interior lumen should be sized as small as possible in order to receive the anchor body and seal the opening. The anchor body of the closure device 310 can be embedded or molded within the center of the plug member 340. One method of making the closure device 310 is to attach two or more hook members as described above with each distal end lying adjacent to one another. The plug member can then slide over the distal end to allow the distal ends to penetrate through the plug member. With the distal ends completely through the plug member, the distal ends can be bent outwardly to a suitable distance and angle. The plug member can then be trapped between the hooks at the proximal and distal ends of the closure device 310.

Figure 9B:
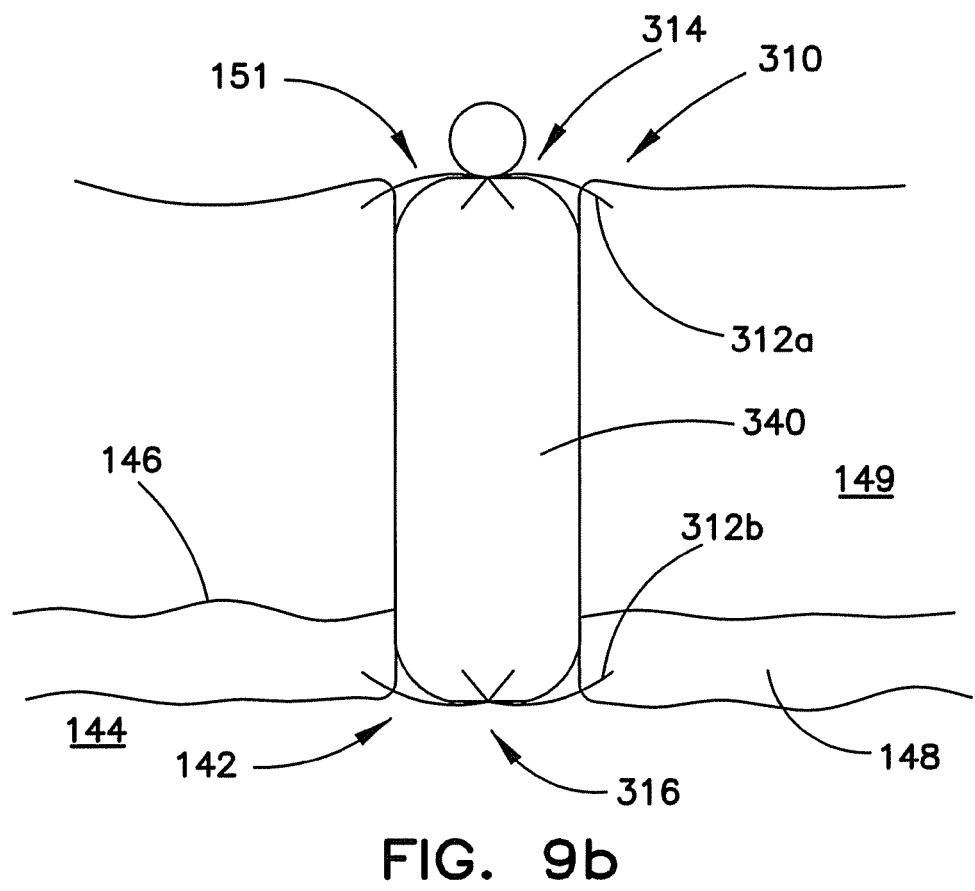
FIG. 9b is a side view depicting the closure device of FIG. 9a delivered to an opening of a body vessel.

In addition to some steps described above related to the delivery of the closure device of the first and second embodiments, with retraction member in the locked position, the pusher can engage with and urge the closure device 310 to exit the distal end of the outer sheath and enter into the interior space of the body vessel. With a proximal portion of the closure device still within the introducer, the hooks and/or barbs at the distal end of the closure device move to the extended configuration when the closure device exits the introducer. The closure device is configured to move outward such that the hooks and/or barbs 312b are positioned at wall tissue beyond or surrounding the opening. The introducer can then be pulled in the proximal direction to allow the hooks and/or barbs 312b of the closure device to engage and penetrate the interior of the body vessel wall. With the retraction member in the unlocked position, the introducer can be removed from contact with the proximal end of the closure device to expose the plug member to sealably contact with the opening of the body vessel and a portion of the channel through the interstitial tissue. The introducer is further removed such that the hooks and/or barbs 312a of the proximal end penetrate the interstitial tissue. Tugging on the retraction member can ensure that the closure device is securably placed in the opening. The retraction member can then be removed from the eyelet of the closure device. FIG. 9b depicts the closure device 310 deployed in the opening 142 of the body vessel 146. Here, the hooks and/or barbs 312a at the proximal end 314 are engaged with the interstitial tissue 149 and the hooks and/or barbs 312b at the distal end 316 are engaged with the vessel wall 148 from the interior space 144. The plug member 340 can substantially fill the opening 142 of the body vessel 146 and a portion of the channel 151 through the interstitial tissue 149.

During closure of the opening in the body vessel with the closure device of the second embodiment, the plug member can sealably engage against the portion surrounding the opening to close the opening in the body vessel. By holding the closure device in place until clotting occurs, closure can occur through the self-healing process or as a result of the clotting. Once closure has been completed, the closure device may be left in the body permanently or be bioabsorbed by the body. The closure device can be supplied in different diameters to accommodate different sizes of catheters and different sizes of the opening.

The various embodiments illustrated in the Figures are non-limiting and various features of one can be incorporated into another embodiment without departing from the scope. Other limitations can include hook members that can be curved or have a wave structure or other design, instead of straight. The hooks of the hook members can include multiple hooks to engage additional portions of the tissue. The hooks can be linear forming a V-shape or curved. The hooks are configured to be sharp in order to penetrate into the vessel in one direction, but not to cut laterally once anchored into the vessel. The hooks may be sized to penetrate only a portion of the body vessel or may penetrate through the entire wall of the body vessel. The hooks may also contain barbed tips that ensure the hooks remain engaged with the body vessel wall during securement of the body vessel.

Wire and/or frame material that make up the hook members of the closure device and/or the tubular member can include biocompatible materials. Examples include non-absorbable alloys and compounds including shape memory alloys, such as Nitinol, stainless steel, such as 304SS, or other comparable metals or compounds, such as MP35, Nickel-Titanium alloy, Kevlar, nylon polyester acrylic, gold, platinum, tantalum, niobium, molybdenum, rhodium, palladium silver, hafnium, tungsten, and iridium. Materials with memory can be useful to allow the hook members to spontaneously open after extended from the outer sheath. These can be made in the form of wires, fibers, filaments, small beams, and other extruded, woven, or formed shapes. Piano wire, super elastic memory wire, chromium allows, alloys of titanium and nickel, and other elastic memory materials previously mentioned as well as others can be used as well.

Preferably, the closure device and/or plug member comprise a biodegradable material that is configured to degrade sooner than the tubular member. Since the hooks of the closure device are biased toward the pre-loaded configuration or extended configuration, if the tubular member degrades sooner, the hooks will tend to expand back to the extended configuration which may adversely affect the healing process. A biodegradable polymer or compounds, such as poly-L-lactide (PLLA), poly(lactic-co-glycolic acid) (PLGA), poly-lactic acid (PLA) or other comparable polymers or even magnesium alloys, may be used for the wire, frame, and/or tubular member. Preferably, the biodegradable materials degrade over about 90 days to about 6 months to allow for sufficient healing of the opening before the degrading of the closure device. It is also desirable the biodegradable materials maintain strength during the first 30 days of healing to permit sufficient and effective healing of the opening. Other types of polymers may be used including flexible polymeric materials with elastomeric properties including polyurethane, polyethylene, polyestenurethane, polyimide, olyethreimide, polycarbonate, polysiloxane, polyvinyls, hydroxyethylmethacrylate, related polymers, co-polymers of these or other polymers, or drug-embedded or drug-eluting polymers to prevent coagulation or intimal hyperplasia (such as paclitaxel), also which can be made radiopaque by markers and addition of appropriate radiopaque.

Examples of the retraction member material can include, but are not limited to, absorbable, non-absorbable, braided, monofilament, pseudo-monofilament, multifilament, barbed, smooth, directional, and bidirectional. The retraction member material can be composed of but not limited to polyglycolic acid, polydioxanon, polylactate, polycaprone, silk, linen, cotton, treated and non-treated collagen, "catgut," chromic, Vicryl, Monocyrl, PDS, polyester, polypropylene, polyamide, stainless steel, and others. The retraction member may also include tubular members formed of biocompatible polymers.

The remodelable material described above in relation to the various embodiments can be ECM, SIS, remodelable or collagenous foam, foamed ECM, lyophilized SIS or vacuum pressed SIS. Some foam collagen is known to expand when absorbing biofluids. In this instant, it is preferable to take advantage of the expandability of the foam collagen to plug and seal the opening. One non-limiting example of a suitable remodelable material is the SURGISIS® BIODESIGN™, commercially available from Cook Incorporated, Bloomington, Ind. Another suitable remodelable material is the graft prosthesis material described in U.S. Pat. No. 6,206,931 to Cook et al., incorporated herein by reference.

Therapeutic agents can be used to promote faster healing and/or clotting of the opening. For example, the wire or frame used for the closure device may be coated with a therapeutic agent with known methods known in the art. For example, the closure device can have members that are coated or backed with a fabric or membrane, either completely or partially. The implanted closure device can elute suitable therapeutic material to prevent thrombogenesis, hemorrhage, inflammation, intimal hyperplasia with vascular closure, and the like.

The therapeutic agent may be an antisense compound which may have: (i) morpholino subunits linked together by phosphorodiamidate linkages, 2 atoms long, joining the morpholino nitrogen of one subunit to the 5' exocyclic carbon of an adjacent subunit; and (ii) a sequence of bases attached to the subunits and containing a therapeutically beneficial antisense nucleotide sequence. While the compound need not necessarily 100% complementary to the target sequence, it is preferably effective to stably and specifically bind to the target sequence such that expression of the target sequence is modulated. The appropriate length of the oligomer to allow stable, effective binding combined with good specificity is about 8 to 40 nucleotide base units, and preferably about 12-25 base units. Mismatches, if present, are less destabilizing toward the end regions of the hybrid duplex than in the middle. Oligomer bases that allow degenerate base pairing with target bases are also contemplated, assuming base-pair specificity with the target is maintained. The compound preferably contains internal 3-base triplet complementary to the AUG site, and bases complementary to one or more bases 5' and 3' to the start site. One preferred compound sequence is the 20 mer having the base sequence: 5'-ACG TTG AGG GGC ATC GTC GC-3', where the CAT triplet in the sequences binds to the AUG start site, the 6 bases 3' to the CAT sequence extend in the upstream (5') direction on the target, and the 11 bases 5' to the CAT sequence extend downstream on the target. This compound has enhanced solubility by virtue of having no self-annealing regions. Preferably, the therapeutic agent is a morpholino antisense compound having (i) from 8 to 40 nucleotides, including a targeting base sequence that is complementary to a region that spans the translational start codon of a c-myc mRNA; and (ii) uncharged, phosphorous-containing intersubunit linkages, in an amount effective to reduce the risk or severity of restenosis in the patient. These therapeutic agents are described in U.S. Pat. No. 7,094,765 and published US patent application US 2006/0269587 A1, which are incorporated herein by reference in their entirety. While the therapeutic agent is described with respect to certain preferred antisense compounds, any suitable therapeutic agent in fluid form (i.e., a gas and/or a liquid) or in a fluid carrier may be delivered from the balloon catheter assembly.

In one embodiment of the invention, the therapeutic agent is an antithrombogenic agent. Devices comprising an antithrombogenic agent are particularly preferred for implantation in areas of the body that contact blood. An antithrombogenic agent is any agent that inhibits or prevents thrombus formation within a body vessel. Types of antithrombotic agents include anticoagulants, antiplatelets, and fibrinolytics. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Another example of an antithrombotic agent is a nitric oxide source such as sodium nitroprussiate, nitroglycerin, S-nitroso and N-nitroso compounds. In one embodiment, a material capable of releasing nitric oxide from blood-contacting surfaces can be delivered by the device of the invention. Examples of such materials include, but are not limited to, those described in U.S. publication number 2004/0224868A1, published Nov. 11, 2004, and 2002/0115559A1, published Aug. 22, 2002, the contents of which are incorporated by reference. Other examples of therapeutic agents suitable for inclusion in the devices of the present invention include antiproliferative/antimitotic agents including natural products such as vinca alkaloids (vinblastine, vincristine, and vinorelbine), paclitaxel, rapamycin analogs, epidipodophyllotoxins (etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) $II_b/III_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i. e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat. Still other bioactive agents that can be incorporated in or coated on a frame include a PPAR α-(alpha) agonist, a PPAR δ (delta) agonist and RXR agonists, as disclosed in published U.S. Patent Application US2004/0073297 to Rohde et al., published on Apr. 15, 2004 and incorporated in its entirety herein by reference.

While these features have been disclosed in connection with the illustrated preferred embodiments, other embodiments of the invention will be apparent to those skilled in the art that come within the spirit of the invention as defined in the following claims.

What is claimed is:

1. A device for closure of an opening formed through a wall of a body vessel of a patient, the device comprising:
    an anchor body having a first end and a second end, the first end including a plurality of hook members each including a tissue engagement structure configured to engage tissue of said body vessel, the second end configured as an eyelet,
    wherein the anchor body is formed of a single continuous wire and is movable between a contracted configuration and an extended configuration, where the anchor body is contractible to fit within said opening, and in the extended configuration the hook members of the anchor body are configured to be displaced outward to a cross-sectional area greater than the cross-sectional area of said opening and the tissue engagement structures of the hook members extend away from a central axis of the anchor body;
    an implantable tubular member having a first end and a second end and a lumen extending therethrough, the second end configured to remain in abutting contact with the body vessel, the lumen sized to receive the anchor body in the contracted configuration, wherein the tubular member is slidably engageable with a portion of the anchor body to urge the anchor body to move from the extended configuration to the contracted configuration;
    a retraction member disposed longitudinally within the lumen of the tubular member and attached to the eyelet of the anchor body, wherein the retraction member is retractable within the lumen of the tubular member to bring the second end of the tubular member closer to the first end of the anchor body;
    a sheath having a proximal end and a distal end, a distal portion of the sheath insertable through said opening, the sheath having a lumen extending therethrough; and
    a pusher disposed within the lumen of the sheath and movable within the sheath lumen; the pusher having a proximal end and a distal end and a lumen extending therethrough;
    wherein the anchor body is contractible to be disposed within the lumen of the sheath, the tubular member is interposed between the distal end of the pusher and the anchor body, and the retraction member has a first portion attached to the anchor body and a second portion extending past the first end of the tubular member.

2. The device of claim 1, wherein the hook members of the anchor body in the extended configuration are disposed about the central axis at an acute angle.

3. The device of claim 1, wherein the hook members of the anchor body in the extended configuration includes a first portion disposed about the central axis at an angle about substantially perpendicular thereto, a second portion disposed parallel to the central axis, and a bend interconnecting the first and second portions.

4. The device of claim 1, wherein the tissue engagement structures of the anchor body are configured to be disposed inside said body vessel and extend toward the second end of the anchor body to penetrate the tissue of said body vessel from inside said body vessel, wherein the hooks are configured to move radially inward such that a portion of an edge of said opening is brought to abut another portion of said opening edge.

5. The device of claim 1, wherein the tubular member includes remodelable material attached to the second end thereof, the remodelable material contactable with said opening.

6. The device of claim 5, wherein the remodelable material includes a lumen configured to have a smaller cross-sectional area than said opening and sized to receive the second end of the anchor body.

7. The device of claim 1, wherein the tubular member has a length sized to receive a portion of the anchor body that is external to said body vessel wall.

8. The device of claim 1, wherein the tubular member is adapted to be positioned external to said body vessel wall.

9. The device of claim 1, wherein the retraction member is lockable to permit manipulation of the anchor body.

10. A device for closure of an opening formed through a wall of a body vessel of a patient, comprising:
    an anchor body defined about a central axis, the anchor body having a first end, a second end, and a bent member therebetween, the first end including a plurality of tissue engagement structures configured to engage tissue of said body vessel, wherein the anchor body is movable between a contracted configuration and an extended configuration, where the anchor body is contractible to fit within said opening, and in the extended configuration the bent member has a first portion angled away from the central axis and a second portion that is substantially parallel with the central axis, and the tissue engagement structures face away from the central axis and are configured to be displaced outward away from the central axis to a cross-sectional area greater than the cross-sectional area of said opening;
    an implantable tubular member disposed about the central axis and having a first end, a second end, and a lumen extending therethrough, the lumen sized to receive the anchor body in the contracted configuration, wherein the tubular member is movable between a first position disposed away from the anchor body and a second position slidably engaging the anchor body, and, in the second position, the tissue engagement structures are positioned outside the lumen of the tubular member to capture the wall of the body vessel between the second end of the tubular member and the tissue engagement structures;
    a retraction member disposed longitudinally within the lumen of the tubular member and removably attached to the anchor body, the retraction member being movable between a locked position and a free position, in the locked position the retraction member is fixed relative to the second end of the anchor body, and in the free position the retraction member is movable relative to the second end of the anchor body in order for the retraction member to be removed;
    a sheath having a proximal end and a distal end, a distal portion of the sheath insertable through said opening, the sheath having a lumen extending therethrough; and
    a pusher disposed within the lumen of the sheath and movable within the sheath lumen; the pusher having a proximal end and a distal end and a lumen extending therethrough;

wherein the anchor body is contractible to be disposed within the lumen of the sheath, the tubular member is interposed between the distal end of the pusher and the anchor body, and the retraction member has a first portion removably attached to the anchor body and a second portion extending past the proximal end of the pusher;

wherein the tubular member is movable along the central axis over the retraction member in the locked position from the first position to the second position for the lumen of the tubular member to slidably engage the first portion of the bent member, whereby the tissue engagement structures are urged to converge inward toward the central axis and cross one another.

11. The device of claim 10, wherein the tubular member and the anchor body comprise a biodegradable material.

12. The device of claim 10, wherein the retraction member is removable from the second end of the anchor body when the tubular member is in the second position.

13. The device of claim 12, wherein the retraction member is a single strand that is looped through the anchor body and removable from the anchor body.

14. The device of claim 10, wherein the retraction member is retractable to bring the first end of the tubular member closer to the first end of the anchor body.

15. A device for closure of an opening formed through a wall of a body vessel of a patient, the device comprising:

an anchor body having a first end and a second end, the first end including a plurality of hook members each including a tissue engagement structure configured to engage tissue of said body vessel, the second end configured as an eyelet, wherein the anchor body is moveable between a contracted configuration and an extended configuration and contractible to fit within said opening of the wall of the body vessel, and, in the extended configuration, the hook members of the anchor body are configured to be displaced outward to a cross-sectional area greater than the cross-sectional area of said opening and the tissue engagement structures of the hook members extend away from a central axis of the anchor body and toward the second end of the anchor body to penetrate an inner surface of the wall of the body vessel;

an implantable tubular member having a first end and a second end and a lumen extending therethrough, the lumen having a diameter sized to receive the anchor body in the contracted configuration and a length sized to extend from the wall of the body vessel to at least the second end of the anchor body to receive a portion of the anchor body that is external to the body vessel when the anchor body is deployed therein, wherein the tubular member is slidably engageable with a portion of the anchor body to urge the anchor body to move from the extended configuration to the contracted configuration;

a retraction member disposed longitudinally within the lumen of the tubular member and removably attached to the eyelet of the anchor body, wherein the retraction member is retractable within the lumen of the tubular member to bring the second end of the tubular member closer to the first end of the anchor body;

a sheath having a proximal end and a distal end, a distal portion of the sheath insertable through said opening, the sheath having a lumen extending therethrough; and a pusher disposed within the lumen of the sheath and movable within the sheath lumen; the pusher having a proximal end and a distal end and a lumen extending therethrough;

wherein the anchor body is contractible to be disposed within the lumen of the sheath, the tubular member is interposed between the distal end of the pusher and the anchor body, and the retraction member has a first portion attached to the anchor body and a second portion extending proximally past the distal end of the pusher.

16. A device for closure of an opening formed through a wall of a body vessel of a patient, comprising:

an anchor body defined about a central axis and formed of a single continuous wire, the anchor body having a first end, a second end, and a bent member therebetween, the first end including a plurality of tissue engagement structures facing away from the central axis and configured to engage tissue of said body vessel, wherein the anchor body is movable between a contracted configuration and an extended configuration, where the anchor body is contractible to fit within said opening, and in the extended configuration the bent member has a first portion extending away from the second end of the anchor body at an angle substantially perpendicular to the central axis and a second portion extending away from the first portion of the bent member and the second end of the anchor body and substantially parallel with the central axis, and the tissue engagement structures are spaced from the second end of the anchor body by a distance along the central axis and are configured to be displaced outward away from the central axis to a cross-sectional area greater than the cross-sectional area of said opening;

an implantable tubular member disposed about the central axis and having a first end, a second end, and a lumen extending therethrough, the lumen sized to receive the anchor body in the contracted configuration, wherein the tubular member is movable along the central axis between a first position disposed away from the anchor body and a second position slidably engaging the anchor body to capture the wall of the body vessel between the second end of the tubular member and the first end of the anchor body, where the tissue engagement structures extend toward the second end of the anchor body to penetrate an inner surface of the captured wall of the body vessel and the second end of the tubular member is configured to engage an outer surface of the captured wall of the body vessel opposite the inner surface;

a retraction member disposed longitudinally within the lumen of the tubular member and removably attached to the anchor body, wherein the retraction member is retractable within the lumen of the tubular member to bring the second end of the tubular member closer to the first end of the anchor body;

a sheath having a proximal end and a distal end, a distal portion of the sheath insertable through said opening, the sheath having a lumen extending therethrough; and a pusher disposed within the lumen of the sheath and movable within the sheath lumen; the pusher having a proximal end and a distal end and a lumen extending therethrough;

wherein the anchor body is contractible to be disposed within the lumen of the sheath, the tubular member is interposed between the distal end of the pusher and the anchor body, and the retraction member has a first portion attached to the anchor body and a second portion extending past the first end of the tubular member.

* * * * *

UNITED STATES PATENT AND TRADEMARK OFFICE
CERTIFICATE OF CORRECTION

| | | |
|---|---|---|
| PATENT NO. | : 8,821,532 B2 | Page 1 of 1 |
| APPLICATION NO. | : 12/363271 | |
| DATED | : September 2, 2014 | |
| INVENTOR(S) | : Schaeffer | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1037 days.

Signed and Sealed this
Fifteenth Day of September, 2015

Michelle K. Lee
*Director of the United States Patent and Trademark Office*